United States Patent [19]

Brooks

[11] Patent Number: Plant 7,140

[45] Date of Patent: Feb. 6, 1990

[54] VARIETY OF TROPICAL MANGO NAMED MARTY

[76] Inventor: Neal P. Brooks, P.O. Drawer 9, 18400 SW. 256 St., Homestead, Fla. 33090

[21] Appl. No.: 155,479

[22] Filed: Feb. 12, 1988

[51] Int. Cl.[4] ..... A01H 5/00

[52] U.S. Cl. ..... Plt./33

[58] Field of Search ..... Plt./33

[56] References Cited

PUBLICATIONS

Register of New Fruit and Nut Varieties, 2nd Edition, Brooks & Olmo, 1972, Univ. of Calif. Press., p. 291.

*Primary Examiner*—Robert E. Bagwill

*Attorney, Agent, or Firm*—Malin, Haley, McHale, DiMaggio & Crosby

[57] ABSTRACT

A new mango cultivar having a large plump fruit. Average weight is 20 to 26 ounces when mature. Flesh is yellow with very little fiber. Seed size small, the shape is flat and is only a small percentage of total fruit weight. Skin is 75% dark purplish red. It has an usuaul smooth texture to the skin that feels different from other mangos.

2 Drawing Sheets

BRIEF SUMMARY OF THE INVENTION

Presented herein is a new variety of tropical mango cultivar which resulted from the selection of seedlings over the years. This new mango has been asexually reproduced by grafting. Scions were budded to seedling trees and other scions were grafted to stumps of other mango trees. The new mango has desirable characteristics that many of the present varieties do not have. The exact parentage of the mango is unknown but it is believed to be a cross between a Tommy Atkins and a Keitt. This mango is characterized by having desirable weight of 20 to 26 ounces, skin color of dark purplish red over light green, a smooth texture of the flesh, small size of seed and good flavor.

BRIEF DESCRIPTION OF THE DRAWINGS

FIG. 1 is a photograph of a tree bearing fruit.

FIG. 2 is a photograph of a whole fruit and a sliced fruit portion. The whole fruit exhibits the darker skin color.

FIG. 3 is a photograph of a number of fruits showing the lighter skin color.

DETAILED DESCRIPTION OF THE PREFERRED EMBODIMENT

Presented herein is a new variety of tropical mango cultivar which results from the proper selection of seedlings over the years. The new mango evolved from a seedling that was selected from a large quantity of seeds that were planted and observed in a cultivated grove. The particular seedling was selected because it had many desirable characteristics that many of the present varieties that are commercially grown in South Florida do not have. The parentage of this new variety is not known. The parentage appears to be a cross between a Tommy Atkins and a Keitt.

This new mango variety has been asexually reproduced. Scions were budded to seedling trees. Other scions were grafted on to stumps of other mango trees.

The characteristics that make this a very desirable variety are the fruit size and color, smooth texture of the flesh, small size of seed and good flavor as set forth below.

The tree and limbs are shown in FIG. 1. The tree is a vigorous upright growing tree. The foliage is of average density and leaves are dark green when mature. Young leaves are dark reddish brown. The tree blooms in Feburary and fruit matures and can be picked in August.

The tree bears a large plump fruit somewhat similar in shape to the Keitt, shown in FIG. 2. Average weight of the new mango is 20 to 26 ounces when mature. The flesh of the new mango shown in FIG. 2 is yellow, portions ranging from 10A trough 10D with very little fiber. Seed size is small, shape is flat and is only a small percentage of total fruit weight. Skin of the new mango shown in FIGS. 2 and 3 ranges from a dark purplish red near mahogany to a deep reddish black. No appropriate color chart values could be found. It has an unusual smooth texture to the skin that feels different from other mangos. Fruit appearance and quality are excellent and the flesh has a pleasant aroma and flavor.

The seed of the instant new variety of mango measures approximately one inch by $\frac{3}{4}$ inch, and the fruit itself at maturity measures approximately five inches long by $3\frac{1}{2}$ inches wide.

The color values expressed herein are those of the R.H.S. Color Chart.

What I claim is:

1. A new and distinct variety of tropical mango substantially as described and illustrated having a fruit characterized by a dark purplish red skin color.

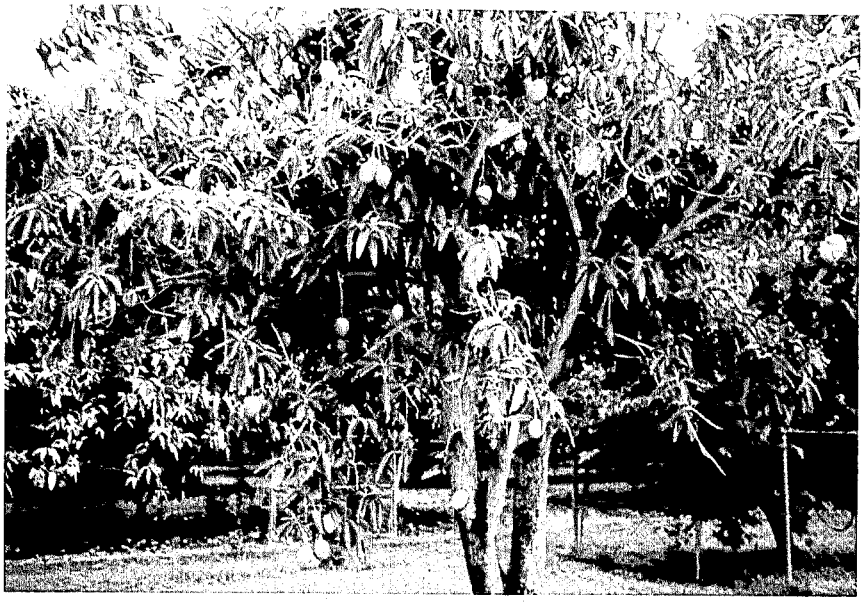
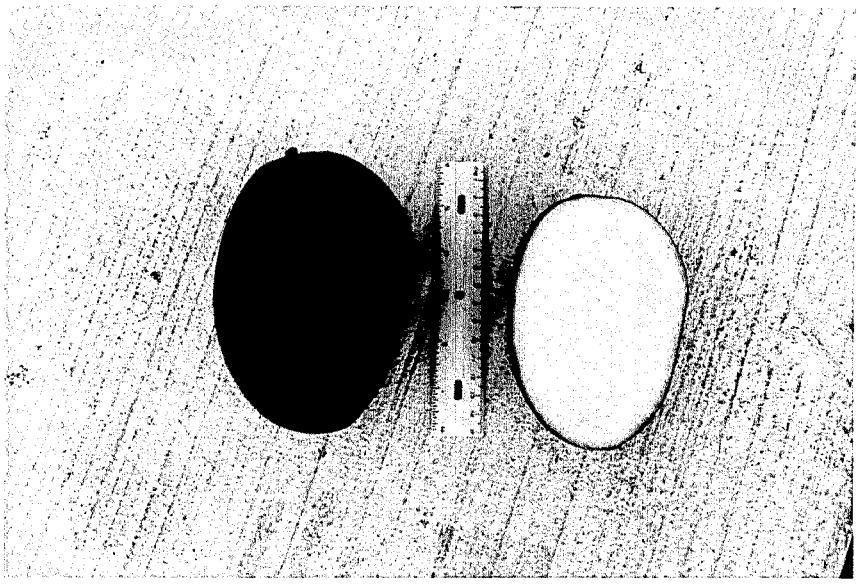

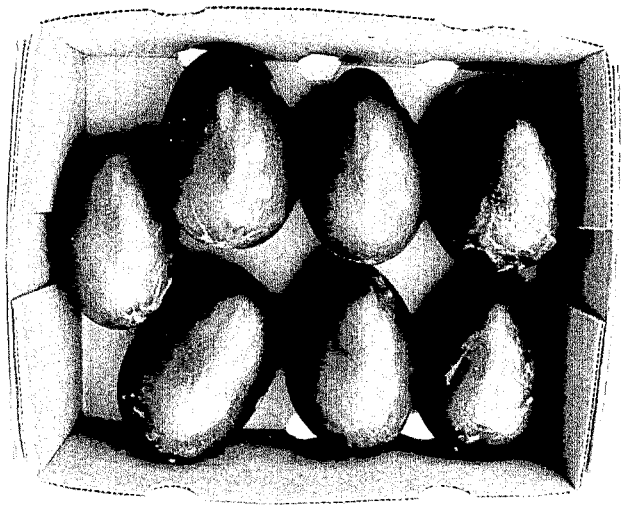

* * * * *